United States Patent [19]

Feringa

[11] Patent Number: 4,661,642

[45] Date of Patent: Apr. 28, 1987

[54] PROCESS FOR THE OXIDATION OF ALPHA-OLEFINS

[75] Inventor: Bernard L. Feringa, Amsterdam, Netherlands

[73] Assignee: Shell Oil Company, Houston, Tex.

[21] Appl. No.: 800,191

[22] Filed: Nov. 21, 1985

[30] Foreign Application Priority Data

Nov. 22, 1984 [GB] United Kingdom ................ 8429538

[51] Int. Cl.[4] ............................................ C07C 45/33
[52] U.S. Cl. ..................................... 568/475; 568/470
[58] Field of Search ................................. 568/470, 475

[56] References Cited

U.S. PATENT DOCUMENTS 4,323,562 3/1982 Tovrog et al. ...................... 568/475
4,521,631 6/1985 Nishimura et al. .................. 568/470

OTHER PUBLICATIONS

Tovrog et al., J. Amer. Chem. Soc., vol. 102 (1980) pp. 6616–6618.
Sndrews et al. J. Amer. Chem. Soc., vol. 103 (1981) pp. 2894–2896.
Henry et al. Publishing Co. (1974) p. 4, Palladium Catalyzed Oxidation of Hydrocarbons.

*Primary Examiner*—Werren B. Lone

[57] ABSTRACT

A process for the oxidation of alpha-olefins having from 3 to about 30 carbon atoms, in which the alpha-olefin and molecular oxygen are contacted in the presence of a solution of a Group VIII metal complex containing at least one $NO_2$ or $NO$ ligand, a divalent copper salt and a tertiary alcohol as solvent.

20 Claims, No Drawings

PROCESS FOR THE OXIDATION OF ALPHA-OLEFINS

The present invention relates to a process for the oxidation of alpha-olefins with molecular oxygen in the presence of Group VIII metal complexes containing at least one $NO_2$ or NO ligand.

The oxidation of alpha-olefins with molecular oxygen in the presence of Group VIII metal complexes containing $NO_2$ or NO ligands has been disclosed. It is known, for instance, to oxidize propene or acetone quantitatively in the presence of a cobalt complex containing $NO_2$ or NO ligands and a divalent palladium compounds as co-catalyst. (cf.: J.A.C.S. 102 (1980) 6616–8). Oxidation of 1-decene with molecular oxygen in the presence of a palladium complex containing $NO_2$ or NO ligands to form 2-decanone is known from J.A.C.S. 103 (1981) 2894–6. Other relevant disclosures of such oxidation processes are found in U.S. Pat. Nos. 4,191,696 and 4,322,562.

In oxidation processes catalyzed by palladium complexes containing $NO_2$ or NO ligands, the formation of ketones is preferent to the formation of aldehydes, which is also the case with most Wacker-type oxidations of alpha-olefins using palladium catalysts. With the exception of styrene, which yields 75% aldehyde, alpha-olefins have produced ketones as the main product accompanied by less than 20% aldehyde (cf.: Palladium Catalyzed Oxidations of Hydrocarbons, P. M. Henry, D. Reidel Publishing Company, 1979, p. 4).

It has now been found that in the oxidation of alpha-olefins with molecular oxygen the selectivity to formation of aldehydes can be increased when the reaction is performed in the presence of a Group VIII metal complex containing a $NO_2$ or NO ligand, a divalent copper salt, and a tertiary alcohol as solvent.

The present invention therefore is a process for the oxidation of an alpha-olefin reactant comprising one or more alpha-olefins having from 3 to about 30 carbon atoms, which comprises contacting the alpha-olefin reactant with molecular oxygen in the presence of a solution of a Group VIII metal complex containing (a) at least one ligand selected from the group consisting of $NO_2$ and NO ligands, (b) a divalent copper salt, and (c) a tertiary alcohol solvent.

The Group VIII metal complexes containing at least one ligand from the group of $NO_2$ and NO ligands to be used in the process of the invention may be complexes of rhodium, palladium, platinum or ruthenium. The use of palladium complexes, in particular palladium II complexes, is preferred.

The complexes may further, optionally, comprise, in addition to the $NO_2$ and/or NO ligands, non-oxidizable ligands (for example, nitrile compounds such as acetonitrile, benzonitrile and isopropylonitrile), heterocyclic aromatic nitrogen compounds (for example, pyridine, bipyridine, terpyridines, phenanthroline, porphyrins, phtalocyanins or N,N-bissalicylidene-O-phenylenediamino). These optional additional ligands are non-oxidizable in the sense that they do not undergo oxidation under conditions of the process. A nitrile compound is preferred as the further ligand.

In particular the complexes are cationic complexes which may comprise anions such as $Br^-$, $Cl^-$, nitrite anions, sulfate anions, phosphate anions, sulfonate anions, $BF_4^-$, $PF_6^-$ or $SbF_6^-$.

Examples of suitable complexes include $[(CH_3CN)_4RhNO_2]^{2+}[BF_4^-]_2$, $[(CH_3CN)_4RhNO]^{2+}[PF_6^-]_2$, $[(CH_3CN)_2Pd(NO_2)Cl]$, $[(CH_3CN)_2Pd(NO_2)_2]$, $[(bipyridine)(CH_3CN)_2RhNO_2]^{2+}[PF_6^-]_2$.

The palladium complexes $(CH_3CN)_2Pd(NO_2)Cl$ and $(CH_3CN)_2Pd(NO_2)_2$ are considered particularly preferred for use in this process.

The complexes used are generally prepared separately but may also be formed in situ in the reaction mixture. Further, it may be useful to add non-oxidizable ligands or nitrites in excess to the amounts in the complexes used.

The amount of Group VIII metal complexes used in the process of the invention is not critical. Catalytic amounts, i.e. those in the range of from 0.01 mmol (millimol) to 10 mmol per mole of alpha-olefin, may be employed, as well as higher amounts.

The divalent copper salts present in the process of the invention may be the copper II halides, preferably the chloride, the copper II carboxylates, preferably the acetate, or the copper II sulfonates, preferably p-toluene sulfonate. The use of copper II chloride is particularly preferred. Generally the divalent copper salts are suitably present in an amount of at least 1 gramatom copper per gramatom palladium. An amount of at least 4 gramatom copper per gramatom palladium is preferred.

The tertiary alcohol solvent in the process of the invention is preferably one or more aliphatic tertiary alcohols, more preferably one or more aliphatic tertiary alcohols having from 4 to about 9 carbon atoms, and most preferably tertiary butanol. The tertiary alcohol may, if desired, be used in admixture with other solvents.

The alpha-olefins with 3 to about 30 carbon atoms which can be oxidized according to the process of the invention, are preferably alpha-olefins with about 6 to 18 carbon atoms. Examples of suitable alpha-olefins are aliphatic olefins in particular linear 1-alkenes, aromatic groups containing olefins such as styrene or substituted olefins such as allyl alcohol.

For the preparation of aldehydes from alpha-olefins the process of the invention represents in principle an alternative to hydroformylation processes.

The process of the invention may be carried out at atmospheric pressure or higher pressures. The temperature may vary from about 0° C. to 150° C. and is preferably in the range of about 30° C. to 80° C.

The process according to the invention is hereinafter illustrated on the basis of a practical example.

EXAMPLES 1–11

A complex $(CH_3CN)_2PdNO_2Cl$ was prepared according to the procedure described in J.A.C.S. 103 (1981) 2894–6. For each of Examples 1–11, a mixture of a specified amount of $(CH_3CN)_2Pd\ ClNO_2$, a specified amount of $CuCl_2 2H_2O$ and specified ml solvent was stirred and heated at 55° C. for 3 hours bubbling slowly dry air through the mixture. The metal salts gradually dissolved to give a yellowish solution which was cooled to 30° C. A specified amount of alpha-olefin was then added and subjected to oxidation during a specified time while bubbling air through the mixture. After the oxidation the reaction mixture was analyzed by gas-liquid chromatography using bromombenzene as an internal standard and by mass spectrometry.

The amounts of the respective reagents employed, the data and the results of Examples 1-11 are given in Table. The yield in mmol is the total of mmol aldehyde plus mmol ketone. The product ratio is the ratio of aldehyde to ketone in % mol.

Also shown in the Table are data and results for two Comparative Examples, designated A and B. These Comparative Examples were performed under the same general procedures as Examples 1-11. However, Comparative Example A was performed without the presence of a copper salt in the solution, and thus not according to the invention. The result of Comparative Example A illustrates that the presence of the copper salt is necessary to obtain selectivity to production of aldehydes. Comparative Example B is not in accordance with the invention in its use of glycol solvent. The results of Comparative Example B illustrate the importance of the specified tertiary alcohol solvent.

addition to ligands selected from the group consisting of $NO_2$ and NO ligands.

5. The process of claim 1, wherein the Group VIII metal complex is $(CH_3CN)_2Pd(NO_2)Cl$.

6. The process of claim 4, wherein the Group VIII metal complex is $(CH_3CN)_2Pd(NO_2)Cl$.

7. The process of claim 1, wherein the Group VIII metal complex is $(CH_3CN)_2Pd(NO_2)_2$.

8. The process of claim 4, wherein the Group VIII metal complex is $(CH_3CN)_2Pd(NO_2)_2$.

9. The process of claim 1, wherein the divalent copper salt is copper II chloride.

10. The process of claim 4, wherein the divalent copper salt is copper II chloride.

11. The process of claim 1, wherein the divalent copper salt is present in an amount of at least about one gramatom copper per gramatom palladium.

12. The process of claim 4, wherein the divalent cop-

TABLE

| EXAMPLE NO. | OLEFIN (MMOL) | SOLVENT | YIELD MMOL | PRODUCT RATIO % MOL | REACTION TIME HRS. | ADDITIONS MMOL | Pd/Cu MMOL |
|---|---|---|---|---|---|---|---|
| 1 | 1-decene (0.41) | t.BuOH | 0.09 | 60/40 | 1.0 | | 0.04/0.18 |
| 2 | 1-decene (0.41) | t.BuOH | 0.28 | 18/82 | 2.06 | | 0.04/0.04 |
| 3 | 1-decene (0.42) | t.BuOH | 0.04 | 70/30 | 3.0 | $KNO_2$ (0.19) | 0.04/0.18 |
| 4 | 1-decene (0.38) | $C_2H_5C(CH_3)_2OH$ | 0.08 | 38/62 | 1.12 | | 0.04/0.18 |
| 5 | 1-decene (0.40) | t.BuOH | 0.11 | 70/30 | 2.0 | | * |
| 6 | styrene (0.85) | t.BuOH | 0.08 | 100/0 | 2.0 | | 0.05/0.20 |
| 7 | 1-octene (0.44) | t.BuOH | 0.19 | 55/45* | 2.52 | | 0.04/0.17 |
| 8 | 4-methyl-pentene-1 (0.77) | t.BuOH | 0.10 | 60/40 | 2.35 | | 0.04/0.27 |
| 9 | 3-methyl-nonene-1 (0.38) | t.BuOH | 0.07 | 18/82 | 3.20 | | 0.05/0.18 |
| 10 | 1-decene | t.BuOH | 0.23 | 50/50 | 3.63 | phenanthroline (0.04) after 1.36 h $A_9BF_4$ (0.21) | 0.05/0.20 |
| 11 | allyl alcohol (0.55) | t.BuOH | 0.40 | 70/30** | 0.5 | | 0.04/0.20 |
| Comparative Example A | 1-decene (0.71) | t.BuOH | 0.02 | 0/100 | 0.15 | | 0.05/0 |
| Comparative Example B | 1-decene (0.84) | glycol | 0.40 | 0/100 | 2.20 | | 0.04/0.28 |

*Pd—$NO_2$ complex prepared according to J.A.C.S. 103 (1981) 2894-6 using isopropylonitrile instead of acetonitrile.
**The reaction mixture comprises 3-t-butoxy-propanal and 3-t.butoxy-2-propenol in a molar ratio of 70/30.

I claim as my invention:

1. A process for the oxidation of an alpha-olefin reactant comprising one or more alpha olefins having from 3 to about 30 carbon atoms to produce corresponding ketones and aldehydes, which comprises contacting the alpha-olefin reactant with molecular oxygen, at a temperature in the range from about 0° to 150° C. and at a pressure of at least one atmosphere, in the presence of a solution of a Group VIII metal complex containing (a) at least one ligand selected from the group consisting of $NO_2$ ligands and NO ligands, (b) a divalent copper salt, and (c) a tertiary alcohol solvent, said Group VIII metal complex being present in a quantity in the range of from 0.01 mmol to 10 mmol per mol of alpha-olefin, and said copper salt being present in a quantity of at least 1 gramatom of copper per gramatom of the Group VIII metal.

2. The process of claim 1, wherein the Group VIII metal complex is a palladium complex.

3. The process of claim 1, wherein the complex comprises a non-oxidizable nitrile compound as a ligand in addition to ligands selected from the group consisting of $NO_2$ and NO ligands.

4. The process of claim 2, wherein the complex comprises a non-oxidizable nitrile compound as a ligand in addition to ligands selected from the group consisting of $NO_2$ and NO ligands.

per salt is present in an amount of at least about one gramatom copper per gramatom palladium.

13. The process of claim 11, wherein the divalent copper salt is present in an amount of at least about four gramatom copper per gramatom palladium.

14. The process of claim 12, wherein the divalent copper salt is present in an amount of at least about four gramatom copper per gramatom palladium.

15. The process of claim 1, wherein the tertiary alcohol solvent comprises one or more aliphatic tertiary alcohols.

16. The process of claim 4, wherein the tertiary alcohol solvent comprises one or more aliphatic tertiary alcohols.

17. The process of claim 15, wherein the alpha-olefins have carbon numbers in the range from about 6 to 18 and the tertiary aliphatic alcohols have from about 4 to 9 carbon atoms.

18. The process of claim 16, wherein the alpha-olefins have carbon numbers in the range from about 6 to 18 and the tertiary aliphatic alcohols have from about 4 to 9 carbon atoms.

19. The process of claim 6 wherein the alpha-olefins have carbon numbers in the range from about 6 to 18, the divalent copper salt is copper II chloride present in an amount of at least 4 gramatom copper per gramatom palladium, and the tertiary alcohol solvent is one or more tertiary aliphatic alcohols having from about 4 to 9 carbon atoms.

20. The process of claim 8, wherein the alpha-olefins have carbon numbers in the range from about 6 to 18, the divalent copper salt is copper II chloride present in an amount of at least 4 gramatom copper per gramatom palladium, and the tertiary alcohol solvent is one more more tertiary aliphatic alcohols having from about 4 to 9 carbon atoms.

* * * * *